United States Patent [19]

Gelbein et al.

[11] Patent Number: 4,585,899

[45] Date of Patent: Apr. 29, 1986

[54] HYDROGENATION OF CARBOXYLIC ACID COMPOUNDS TO ALDEHYDES USING $MNO_2$ ON GAMMA ALUMINA AS CATALYST

[75] Inventors: Abraham P. Gelbein, Morristown; Robert Hansen, West Caldwell, both of N.J.

[73] Assignee: Chem Systems Inc., Tarrytown, N.Y.

[21] Appl. No.: 693,245

[22] Filed: Jan. 22, 1985

[51] Int. Cl.[4] .............................................. C07C 45/41

[52] U.S. Cl. .................................... 568/435; 568/484; 502/324

[58] Field of Search ................................ 568/435, 484

[56] References Cited

U.S. PATENT DOCUMENTS

| | | | |
|---|---|---|---|
| 3,935,265 | 1/1976 | Feinstein et al. | 568/435 |
| 4,093,661 | 6/1978 | Trecker et al. | 568/435 X |
| 4,328,373 | 5/1982 | Strojny | 568/435 |

FOREIGN PATENT DOCUMENTS

| | | | |
|---|---|---|---|
| 0101111 | 2/1984 | European Pat. Off. | 568/484 |

*Primary Examiner*—Bernard Helfin
*Attorney, Agent, or Firm*—Bert J. Lewen; Henry Sternberg

[57] ABSTRACT

A process for selectively forming aldehydes which comprises hydrogenating a carboxylic acid or a carboxylic acid ester in the presence of a manganese catalyst supported on an activated alumina.

11 Claims, No Drawings

HYDROGENATION OF CARBOXYLIC ACID COMPOUNDS TO ALDEHYDES USING $MNO_2$ ON GAMMA ALUMINA AS CATALYST

BACKGROUND OF THE INVENTION

The catalytic vapor-phase hydrogenation of carboxylic acids and esters to form the corresponding aldehydes is well known. Hydrogenation processes wherein the carboxylic acids and esters are free of hydrogen on the alpha-carbon, such as benzoic acid and methyl benzoate, are taught in U.S. Pat. No. 4,328,373, issued on May 4, 1982 to Dow Chemical Company. The reaction is performed in the presence of metal oxide catalysts such as oxides of yttrium, zirconium, cerium, praseodymium, thorium and uranium supported on alpha-alumina. The first two oxides are most preferred. This work is also described in King et al., "An In Situ Study of Methyl Benzoate and Benzoic Acid Reduction on Yttrium Oxide by Infrared Spectroscopic Flow Reactor," *Journal of Catalysis* 76, 274–284 (1982).

U.S. Pat. No. 4,093,661, issued June 6, 1978 to Union Carbide Corporation, shows the vapor phase disproportionation of lower alkanoate esters of alcohols in the vapor phase to produce aldehydes and ketones over metal oxide catalysts. The preferred catalysts include nickel oxide, zinc oxide, and chromium oxide. The use of other metal oxides, namely, oxides of copper, titanium, vanadium, manganese, iron and cobalt, are also disclosed. It is further taught that the catalyst can be supported on an inert catalyst support such as alumina, silica and carbon.

In U.S. Pat. No. 2,018,350, issued on Oct. 22, 1935 to General Aniline Works, Inc., aldehydes are formed from dicarboxylic acids or their anhydrides with reducing gas in the presence of catalysts such as chromium, iron, copper, manganese, cobalt or their oxides, either alone or mixed with each other. Mixtures of such catalysts with other elements such as lead, cerium, uranium or zinc or oxides of these elements are also generally disclosed. The catalysts include granules of pumice impregnated with iron salts and reduced with hydrogen to prepare benzaldehyde from phthalic anhydride. In addition, a catalyst prepared by reducing fragments of ferric oxide activated with chromium compounds is also described. Other catalysts include copper and iron deposited on granular pumice, a reduced mixture of lead oxide, chromium oxide, and iron oxide, and reduced zinc chromate.

SUMMARY OF THE INVENTION

This invention relates to the catalytic vapor-phase hydrogenation of carboxylic acids and esters to form corresponding aldehydes with a manganese catalyst supported on activated alumina. Such alumina include gamma, beta, and eta alumina. The use of the activated alumina support substantially enhances the catalytic activity. These supports are characterized by high surface area, i.e., 2 to 1000 $m^2/g$., preferably from 100 to 500 $m^2/g$., and high pore volume, i.e., 0.3 to 1.0 cc/g. The use of such supports in conjunction with a manganese component provides catalysts that are are particularly useful for converting carboxylic acids and their esters free of hydrogen on their alpha carbon to aldehydes. These catalysts exhibit substantially enhanced activity and selectivity over the prior art. An example of the reaction for which the catalyst of the invention may be used is the conversion of benzoic acid and methyl benzoate to benzaldehyde. Acids having hydrogen on alpha carbons such as acetic acid and butyric acid are not selectively converted with the activated alumina supported manganese catalyst of the invention.

DETAILED DESCRIPTION OF THE INVENTION

Carboxylic acids and esters thereof which can be converted to aldehydes in accordance with the instant invention may be either mono- or dicarboxylic. The esters include aryl and lower alkyl esters of such carboxylic acids. Both aliphatic carboxylic acids and aromatic carboxylic acids may be reacted.

Aromatic carboxylic acids and esters include benzoic, phthalic, isophthalic and terephthalic, as well as alkyl, alkoxy and halo-substituted benzoic acids and esters such as toluic, ethylbenzoic, fluorobenzoic, chlorobenzoic, bromobenzoic and methoxybenzoic. Preferably, the alkyl-substitution would contain from 1 to 6 carbon atoms. Generally, from 1 to 5 alkyl substitutions may be present. Other materials which may be converted include naphthoic, biphenylcarboxylic, anthranoic, trimethylacetic and trifluoroacetic acids and esters.

The supported manganese catalyst may be readily prepared by immersing the support in an aqueous solution of a manganese salt. The manganese salt solution loaded support is then heated at a temperature of from 200° to 500° C. under oxidizing conditions to form supported manganese dioxide. Generally, from 2 to 20 wt. % of the catalyst is added to the support.

Prior to the reduction of the carboxylic acid or carboxylic acid ester, it is preferable to reduce the catalyst to its metallic form in situ under the reaction conditions.

The hydrogenation reaction may be carried out in a batch or a continuous flow system, as will be readily understood by those skilled in the art. The temperature of the reaction may range from 350° to 500° C., preferably from 400° to 450° C. Pressures of from 200 mm Hg up to a high as 100 atm. may be used, though 1 to 5 atm. is preferred.

The molar ratio of the hydrogen to the carboxylic acid or the carboxylic acid ester may range broadly from 1:1 to 1,000:1, preferably from 20:1 to 200:1. The optimum conditions of temperature, pressure and hydrogen concentration may be readily determined by those skilled in the art, depending on the particular reactant being employed.

The rate of flow of the reactants over the catalyst may range from 0.05 to 2.0 kg acid per kg catalyst/hr., preferably from 0.1 to 1.0 kg acid per kg catalyst/hr.

The following examples further illustrate the instant invention:

EXAMPLE 1

Catalysts were prepared by immersing various supports in an aqueous solution of manganese nitrate. The solution and support were heated so as to reflux the solution at about 100° C. for two hours. After cooling to room temperature, the excess solution was decanted and the impregnated support was dried at about 120° C. and calcined at 450° C. to produce the manganese dioxide. A catalyst loading of from about 10 to 20 wt. % of the oxide is easily achieved by this procedure. The catalysts in oxide form were reduced in the reactor at reaction conditions prior to the addition of the feed.

In the reactor system, the organic reactant was first placed in a constant temperature vaporizer. The hydrogen reducing gas was preheated and sparged into a reservoir of the heated reactants. From vapor pressure data, the desired concentration of organic reactant in hydrogen was determined. The hydrogen stream, saturated with organic reactant, was immediately heated to the reaction temperature and passed over the catalysts. The products exiting from the reactor were condensed and collected for analysis.

The following table shows the comparative results obtained. Run No. 1 demonstrates the use of the manganese dioxide catalyst supported on ⅛" gamma-alumina in accordance with the invention. Run Nos. 2 and 3 show comparative runs using the same catalyst supported on 8–12 mesh silica gel and ⅛" alpha-alumina spheres, respectively. The residence times were measured at reaction conditions on an empty tube basis.

TABLE

| Run # | 1 | 2 | 3 |
|---|---|---|---|
| Reactor Volume (cc) | 8.2 | 8.0 | 9.0 |
| Catalyst Charge (gram) | 5.00 | 3.55 | 7.35 |
| Catalyst, % $MnO_2$ | 15.9 | 18.6 | 14 |
| Support Pore Volume, cc/g. | 0.92 | 1.0 | 0.8 |
| Support Surface Area, $m^2/g$. | 194 | 300 | <1 |
| Residence Time (seconds) | 0.62 | 0.79 | 0.60 |
| F/W (Kg Feed/Kg Catalyst-Hr.) | 0.426 | 0.47 | 0.334 |
| Reactor Temp. ° C. | 433 | 435 | 434 |
| Feed: Mole % Benzoic Acid in $H_2$ | 2.1 | 1.80 | 1.8 |
| % Conversion of Benzoic Acid | 91 | 63 | 72.1 |
| % Molar Selectivity to: | | | |
| Benzaldehyde | 94.8 | 55 | 72.5 |
| Benzene | 3.6 | 44 | 27 |
| Toluene | 0.9 | 0.5 | 0.3 |
| Benzyl Alcohol | 0.7 | 0.5 | 0.2 |

It will be noted in Run No. 1 that the conversion of benzoic acid was considerably higher than in Run Nos. 2 and 3. That the support would have this marked effect is quite unexpected. Even more surprisingly, by using the gamma-alumina supported manganese catalyst of the invention a substantially higher molar selectivity to benzaldehyde was obtained. By-product formation in Run No. 1 is manyfold less than in Run Nos. 2 and 3.

EXAMPLE 2

A procedure described in Run No. 1 is followed, except that the feed is methyl benzoate. In a 2 hour run at 430° C., and with a feed stream containing 2.0% methyl benzoate, a conversion of 92% of the methyl benzoate is noted. The selectivity to benzaldehyde is 83%.

EXAMPLE 3

The catalyst described in Run No. 1 is employed in a 5 hour run with p-methylbenzoic acid at 425° C. The conversion is 91% and the selectivity to p-methylbenzaldehyde is 86%.

EXAMPLE 4

The catalyst described in Run No. 1 is employed in a 10 hour run with p-tert-butylbenzoic acid at 430° C. The conversion is 95% with a selectivity to p-tert-butylbenzaldehyde of 86%.

EXAMPLE 5

The catalyst described in Run No. 1 is employed in a 4 hour run with 3,5-dimethylbenzoic acid at 435° C. The conversion is 87% at a 2.7% feed, with a selectivity to 3,5-dimethylbenzaldehyde of 83%.

EXAMPLE 6

The catalyst described in Run No. 1 is employed in a 5 hour run with methyl p-methylbenzoate at 430° C. The conversion is 85%, and the selectivity to p-methylbenzaldehyde 85%.

EXAMPLE 7

The catalyst described in Run No. 1 is employed in a 5 hour run with methyl p-methoxybenzoate at 420° C. The conversion is 87%. The selectivity to p-methoxybenzaldehyde and to anisole is 12% and 75%, respectively.

EXAMPLE 8

The catalyst described in Run No. 1 is used in a 2 hour test with p-fluorobenzoic acid at 430° C. The conversion is 75%, and the selectivity to p-fluorobenzaldehyde 89%.

EXAMPLE 9

The catalyst described in Run No. 1 is used in a 4 hour test with 4-phenylbenzoic acid at 433° C. The conversion is 92%, and the selectivity to p-phenylbenzaldehyde 84%.

EXAMPLE 10

The catalyst described in Run No. 1 is used in a 4 hour test of trimethylacetic acid at 423° C. The conversion is 78%, and the selectivity to trimethylacetaldehyde 72%.

EXAMPLE 11

The catalyst described in Run No. 1 is used in a 10 hour test with dimethylterephthalate at 435° C. The conversion is 89%, and the selectivity to terephthalaldehyde 79%.

We claim:

1. A process for the hydrogenation of an aromatic or aliphatic carboxylic acid or an ester thereof to the corresponding aldehyde, said carboxylic acid or ester being free of alpha hydrogens, which comprises reacting said carboxylic acid or ester with at least a 1:1 molar ratio of hydrogen at a temperature in the range of from 300° to 500° C. and at a pressure of from 200 mm Hg to 100 atm. in the presence of a manganese dioxide catalyst supported on a gamma-alumina.

2. The process of claim 1 wherein the catalyst comprises from 2 to 20 wt. % based on the weight of the gamma-alumina.

3. The process of claim 1 wherein the reactant is benzoic acid or methyl benzoate and the aldehyde produced therefrom is benzaldehyde.

4. The process of claim 1 wherein the reactant is p-methylbenzoic acid or p-methylbenzoate and the aldehyde is p-methylbenzaldehyde.

5. The process of claim 1 wherein the reactant is p-tert-butylbenzoic acid and the aldehyde is p-tert-butylbenzaldehyde.

6. The process of claim 1 wherein the reactant is 3,5-dimethylbenzoic acid and the aldehyde is 3,5-dimethylbenzaldehyde.

7. The process of claim 1 wherein the reactant is methyl p-methyoxybenzoate and the aldehyde is p-methoxybenzaldehyde and anisole.

8. The process of claim 1 wherein the reactant is p-fluorobenzoic acid and the aldehyde is p-fluorobenzaldehyde.

9. The process of claim 1 wherein the reactant is 4-phenylbenzoic acid and the aldehyde is p-phenylbenzaldehyde.

10. The process of claim 1 wherein the reactant is trimethylacetate and the aldehyde is trimethylacetaldehyde.

11. The process of claim 1 wherein the reactant is dimethylterephthalate and the aldehyde is terephthalaldehyde.

* * * * *